United States Patent
Liu et al.

(10) Patent No.: US 9,776,224 B2
(45) Date of Patent: Oct. 3, 2017

(54) METHOD OF UTILIZING REFUSES IN URBAN AND RURAL

(75) Inventors: Guotian Liu, Weifang (CN); Mingquan Zhang, Weifang (CN); Ming'en Hu, Weifang (CN)

(73) Assignee: WEIFANG JINSIDA INDUSTRIAL CO. LTD., Weifang (CN)

( * ) Notice: Subject to any disclaimer, the term of this patent is extended or adjusted under 35 U.S.C. 154(b) by 197 days.

(21) Appl. No.: 13/992,113

(22) PCT Filed: Apr. 2, 2011

(86) PCT No.: PCT/CN2011/072418
§ 371 (c)(1),
(2), (4) Date: Jun. 6, 2013

(87) PCT Pub. No.: WO2012/075756
PCT Pub. Date: Jun. 14, 2012

(65) Prior Publication Data
US 2013/0252314 A1  Sep. 26, 2013

(30) Foreign Application Priority Data
Dec. 9, 2010 (CN) .......................... 2010 1 0581262

(51) Int. Cl.
*B09B 3/00* (2006.01)
*C12P 5/02* (2006.01)
(Continued)

(52) U.S. Cl.
CPC .................. *B09B 3/00* (2013.01); *B03C 1/28* (2013.01); *B03C 1/30* (2013.01); *C05F 9/00* (2013.01);
(Continued)

(58) Field of Classification Search
None
See application file for complete search history.

(56) References Cited

U.S. PATENT DOCUMENTS 3,933,577 A * 1/1976 Penque .............................. 162/4
4,785,622 A * 11/1988 Plumley ....................... 60/39.12
(Continued)

FOREIGN PATENT DOCUMENTS

CA  2258254 A  *  6/2000
CA  2258254 A1     6/2000
(Continued)

OTHER PUBLICATIONS

Yaman, Energy Conversion and Management 45:651-671, 2004.*
(Continued)

*Primary Examiner* — Jennifer Pitrak McDonald
*Assistant Examiner* — Qing Xu
(74) *Attorney, Agent, or Firm* — Nixon Peabody LLP

(57) ABSTRACT

The present invention discloses a method of utilizing refuses in urban and rural areas. The method includes a refuses collection step, a refuse distributing step, a primary magnetic separation step, a primary crushing step, a primary elutriation and floatation step, a uniform cutting step, an acidification and anaerobic treatment step, a selection and separation step, a buffering and adjusting step, an additional anaerobic treatment step and a sludge sedimentation and concentration step. The present invention can make the anaerobic treatment method continuatively dispose the refuses, thereby thoroughly solving the problem that non-anaerobic refuses such as waste plastics, water fiber etc. can not be recycled and completely recycling resources in the refuses.

14 Claims, 1 Drawing Sheet

(51) Int. Cl.
    *B03C 1/28*    (2006.01)
    *B03C 1/30*    (2006.01)
    *C10L 5/46*    (2006.01)
    *C05F 9/00*    (2006.01)
    *C05F 17/00*   (2006.01)
    *C02F 11/04*   (2006.01)

(52) U.S. Cl.
    CPC ............ *C05F 17/0027* (2013.01); *C10L 5/46* (2013.01); *C12P 5/023* (2013.01); *C02F 11/04* (2013.01); *C10L 2290/02* (2013.01); *C10L 2290/06* (2013.01); *C10L 2290/26* (2013.01); *C10L 2290/28* (2013.01); *C10L 2290/40* (2013.01); *C10L 2290/54* (2013.01); *C10L 2290/545* (2013.01); *Y02E 50/10* (2013.01); *Y02E 50/30* (2013.01); *Y02E 50/343* (2013.01); *Y02P 20/145* (2015.11); *Y02W 10/23* (2015.05); *Y02W 30/43* (2015.05); *Y02W 30/47* (2015.05); *Y02W 30/521* (2015.05); *Y02W 30/523* (2015.05); *Y02W 30/524* (2015.05); *Y02W 30/526* (2015.05); *Y02W 30/54* (2015.05); *Y02W 30/62* (2015.05)

(56) References Cited

U.S. PATENT DOCUMENTS

| | | | | |
|---|---|---|---|---|
| 2002/0079266 | A1* | 6/2002 | Ainsworth | C02F 3/28 210/603 |
| 2010/0317090 | A1* | 12/2010 | Parry | 435/262 |
| 2011/0117620 | A1 | 5/2011 | Rietzler | |

FOREIGN PATENT DOCUMENTS

| | | | |
|---|---|---|---|
| CN | 1394701 | | 2/2003 |
| CN | 1394701 | A * | 2/2003 |
| CN | 1431159 | A | 7/2003 |
| CN | 2585865 | Y | 11/2003 |
| CN | 101134684 | A | 3/2008 |
| CN | 101337838 | A | 1/2009 |
| DE | 102008032409 | A1 | 1/2010 |
| EP | 0092882 | A1 | 11/1983 |
| EP | 1275443 | A2 | 1/2003 |
| FR | 2924441 | A * | 6/2009 |
| JP | S 55-015923 | | 2/1980 |
| JP | S55155782 | A | 12/1980 |
| JP | S 58-133897 | | 8/1983 |
| JP | 2002-355654 | | 12/2002 |
| JP | 2004-122073 | | 4/2004 |
| JP | 2005-270950 | | 10/2005 |
| JP | 2007-216168 | | 8/2007 |
| JP | 2009-045612 | | 3/2009 |
| WO | WO02070635 | A2 | 9/2002 |
| WO | WO03004423 | A1 | 1/2003 |
| WO | WO2007068446 | A1 | 6/2007 |

OTHER PUBLICATIONS

Lisa Bolin, et al., LCA of Biogas Through Anaerobic Digestion from the Organic Fraction of Municipal Solid Waste (OFMSW) Compared to Incineration of the Waste, 2009, Proceedings of Eco Design 2009: $6^{th}$ International Symposium on Environmentally Conscious Design and Inverse Manufacturing, Linköping University Post Print, (est. Jan. 1, 2009), (7 pages).

European Search Report corresponding to co-pending European Patent Application No. PCT/CN2011072418, dated May 12, 2015; (6 pages).

International Search Report of International Application No. PCT/CN2011/072418, dated Sep. 15, 2011, 6 pages.

Written Opinion of International Application No. PCT/CN2011/072418, dated Sep. 15, 2011, 4 pages.

* cited by examiner

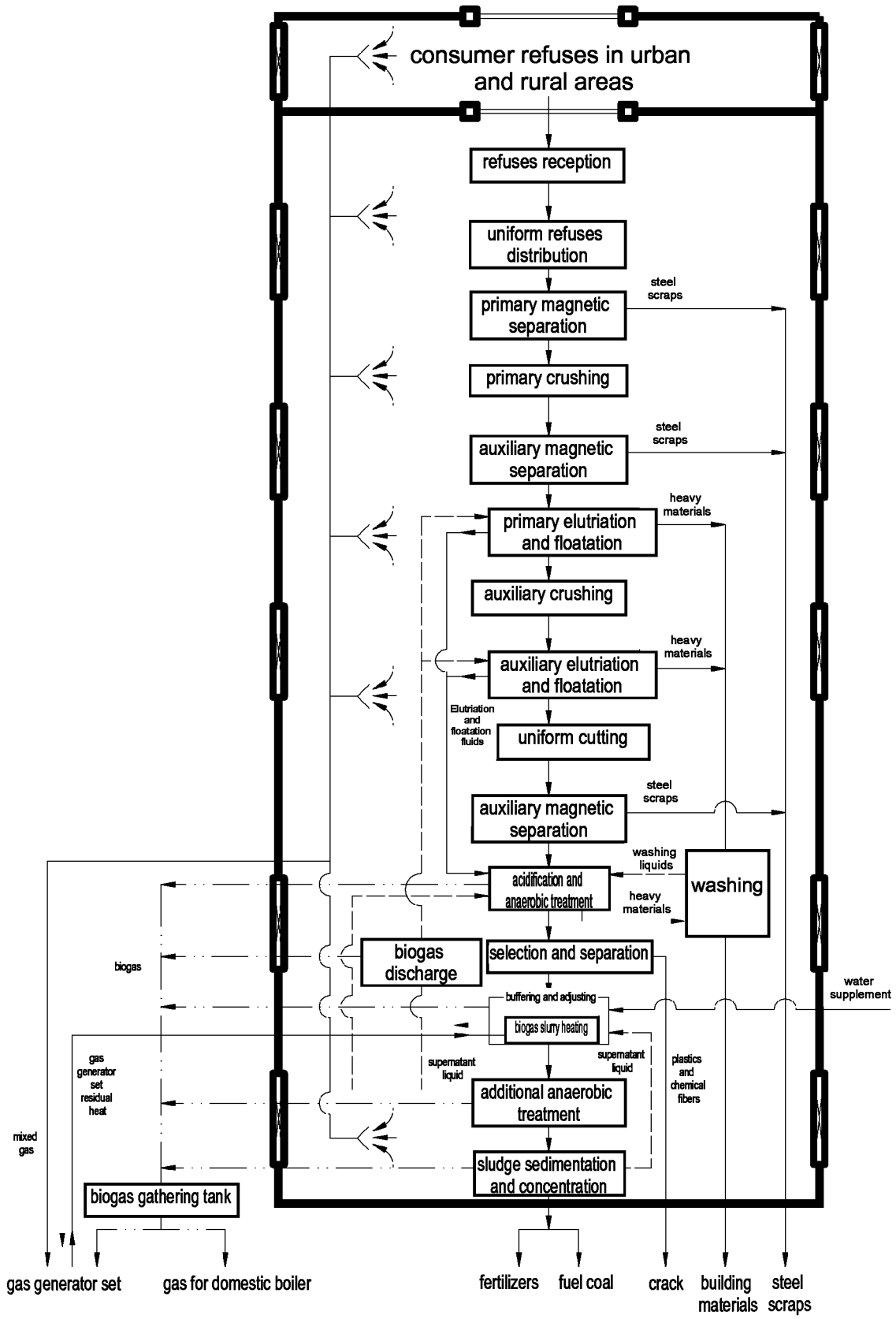

METHOD OF UTILIZING REFUSES IN URBAN AND RURAL

CROSS-REFERENCE TO RELATED APPLICATIONS

This application is a U.S. national stage of International Patent Application No. PCT/CN2011/072418, filed Apr. 2, 2011, which claims priority to Chinese Patent Application No. 201010581262.3 filed Dec. 9, 2010, the contents of which are each incorporated herein by reference in its entirety.

BACKGROUND

1. Field of the Invention

The present invention relates to a resource utilizing method of refuses so as to remove the refuses such as consumer wastes in urban and rural areas.

2. Relevant Background

Along with social progress, sustainable development has become the goal of the human pursuit. Refuses as the products of human activities have not only become the burden of the earth but also the serious impediment to development of the society. The average annual growth rate of the refuses in the world is 8.42% and that in China is up to 10%. 0.49 billion tons of refuses are produced in the world each year. China alone produces nearly 0.15 billion tons of municipal consumer wastes each year. The accumulated amount of municipal consumer wastes in China has been up to 7 billion tons.

In terms of resource utilization, consumer refuses in urban and rural areas may be classified into two categories. The first category may be called anaerobic decomposition refuses, which consist of the perishable and biodegradable organic matters with higher moisture content and include kitchen garbage, waste wood, waste cotton, waste cotton fabric and so on. Waste pollution mainly results from these refuses, wherein the resources are combustible gases and plant fertilizers. The second category may be called non-anaerobic decomposition refuses, which include recyclable materials such as waste plastics, steel scraps and the like and a small part of earth, ashes, glass, ceramics, construction wastes, etc., wherein the resources are steel scraps, plastics, chemical fibers and so on.

Since the anaerobic decomposition refuses in the organic matters are rich in protein, fat and carbohydrate compounds, $NH_3$, $H_2S$ and harmful hydrocarbon gas may be produced during the microbial decomposition process of the organic matters at the normal temperature. These gases have strong odor and toxicity, and directly endanger human. A refuse dump is the place where mosquitoes, flies, rats and insects breed, and is the source of infection of malaria, schistosomiasis, encephalitis B, cholera, viral hepatitis A, dysentery, typhoid fever, hepatitis, plague, leptospirosis and blood-sucking insects' disease. If refuses are piled up casually, $CO_2$, $CH_4$ and the harmful gas $H_2S$ may be produced due to the biological action, which may further lead to explosion. Harmful substances in the refuses continue to pollute air, soil and water, and further intrude into the human body via air, soil, water and food as the media or carrier, damaging human health.

The waste disposal methods in the art are as follows.

Now, landfill and incineration are the most commonly used methods of municipal consumer wastes treatment in the world.

1. Landfill

Landfill is a waste treatment method that is used mostly. Its principle is to dump the wastes to a certain height in a given site covered with covering materials so as to make them reach a steady state after long-term physical, chemical and biological actions. Specific methods include a natural stacking method and a sanitary landfill method. The natural stacking method is simple and easy to be carried out, but causes serious environmental pollution. Since the natural stacking method causes serious and long-term pollution of soil and groundwater, it is a negative emergency measure. The sanitary landfill method is a commonly used method of processing a large amount of urban and rural consumer wastes at present. Countries in the world generally adopt the sanitary landfill method. The shortcomings of this method are large occupation area, complex engineering organization and low degree of harmless processing and volume reduction. There is a potential threat of secondary pollution. In particular, the produced biogas is not easy to diffuse, prone to explosion, which may render the resources in the refuses to be wasted. During the operation, odor is produced. Landfill site is often far from the down town, leading to much more transportation cost. The selection of landfill site is also greatly restricted. This method is likely to cause pollution of earth surface and groundwater.

2. Incineration

Incineration is a waste treatment process in which the wastes as solid fuels are put into the incinerator and then the combustible components thereof are intensively reacted with the oxygen in the air at high temperature. During this process, heat is generated and the wastes are turned into combustion gases with high temperature and a small quantity of the solid residues with stable nature. The advantage of incineration is in that a good volume reduction is reached. The volume can be reduced more than 90% and the weight thereof can be reduced more than 80% as the result of residues, obtaining a relatively thorough treatment. The disadvantage of incineration is destruction of resources. The wastes contain about 70% moisture. Aqueous organic matters consume energy and combustible wastes release energy. During incineration, consumed energy neutralizes released energy, and thus residual energy is very little or negative. Therefore, the calorific value of the wastes is highly required. Further, the consumption of fuels, such as coal and oil, wastes a lot of recyclable resources and chlorinated dibenzo dioxins (PCDD) and chlorinated dibenzofurans (PCDF) are produced during incineration, causing air pollution.

In view of the above, refuses are still treated as wastes. This tendentious concept directs people to adopt the above mentioned waste treatment methods, which results in piled up refuses and seriously impacts on human living space.

The inventor considers that the refuses are the most potential for development and inexhaustible resources. Refuses can become a new starting point of the cycle of resources and an important part of the recycling economy. Organic wastes are above 60%-70% of the municipal consumer wastes and are valuable resources. Recently, as the life level of the people improves, the proportion of the organic wastes in the refuses rises. In-depth understanding of the refuses and deepening are important guiding principles for the discovery of handling the refuses in a right way.

Treatment of municipal organic wastes by an anaerobic fermentation method is an effective method for recycling consumer wastes. Recently, various countries in the world have done much research in terms of biogas generation technology related to waste treatment. For example, the United States and other European countries generally utilize the two-step fermentation and extraction method to study municipal waste anaerobic fermentation so as to produce biogas. China also adopts the anaerobic dry fermentation method to deal with municipal wastes, wherein the produced biogas is used as fuel and the fermented organic wastes turn into organic fertilizer.

In the art, the existing anaerobic fermentation method has the following disadvantages:

1. Either the two-step fermentation and the extraction method or the anaerobic dry fermentation method needs to first perform classification of refuses before processing. This is the biggest bottle neck of restricting waste treatment, thereby resulting in poor utility and huge processing cost of the above mentioned methods. Furthermore, the process is not performed thoroughly, and is not suitable for large-scale application.

2. Intermittent anaerobic treatment restrains waste disposal capacity of the waste treatment plant, and thus a larger area is necessary, which cannot adapt to the waste treatment capacity in modern cities at all.

3. Waste plastics, waste fibers and other non-anaerobic wastes in the refuses cannot be recycled, and are hard to be sorted, which causes a tremendous waste.

SUMMARY

The problem to be solved by the invention is to provide a resource utilizing method of refuses. This method does not require pre-sorting of the refuses. Rather, refuses separation and resource utilization are simultaneously performed and the refuses are continuously disposed.

In order to solve the said problem, the invention provides a resource utilizing method of refuses in urban and rural areas, wherein an acidification and anaerobic treatment tank, an additional anaerobic treatment tank, a biogas gathering tank and a gas generator set are provided and wherein a gas inlet of said gas generator set is connected to the biogas gathering tank through pipes, and the method comprises the following steps:

refuses reception step of unloading refuses collected into a refuses hopper or a refuses silo;

uniform refuses distribution step of uniformly transferring the refuses in the refuses hopper or the refuses silo to subsequent procedures in order to ensure the subsequent procedures to be carried out continuously and to prevent the blocking or interruption of the subsequent procedures; wherein garbage bags in the refuses hopper or the refuses silo are torn, large waste plastics, waste timbers, textile wastes are torn and cut and inorganic wastes which are not able to be torn as well as organic wastes are separated from the refuses; then, the torn and cut refuses are uniformly transferred to the next step; the volume of the processed solid wastes in this step is guaranteed to meet the requirements of a crusher in a primary crushing step;

primary magnetic separation step of magnetically separating the refuses transferred from the above step; wherein steel scraps are separated from the refuses to facilitate the subsequent crushing process and to prevent steel scraps from damaging the crusher in the primary crushing step, and wherein the steel scraps are recycled;

primary crushing step of crushing the refuses transferred from the above step; wherein waste plastics and waste textiles are cut into pieces, steel scraps covering solid wastes are separated and some organic wastes are crushed into slurry; wherein the solid wastes become smaller so that they may be conveyed by a sediment conveying means in a primary floatation step and waste plastics and waste textiles are guaranteed to be screened and separated in the subsequent procedures;

primary elutriation and floatation step of putting the refuses transferred from the above step into a primary elutriation and floatation pool and performing aeration and elutriation; wherein the solid wastes with larger specific gravity at the bottom of the elutriation and floatation pool are transferred into a sediment washing device by a sediment conveying means and are recycled after washing; the wastes with smaller specific gravity in the elutriation and floatation pool are transferred into the next step by a floats conveying means; and the primary elutriation and floatation fluids containing the organic wastes slurry are conveyed to the acidification and anaerobic treatment tank through pipes;

uniform cutting step of further cutting the wastes with smaller specific gravity from the above step so that long strips of the wastes are fully cut into pieces; or selecting and cutting the long strips of the wastes in the wastes with smaller specific gravity transferred from the above step into pieces so as to avoid the pipes to be blocked during the material transportation in the subsequent steps and to ensure the effective separation of plastics and chemical fibers after acidification and anaerobic treatment;

acidification and anaerobic treatment step of transferring the refuses from the above step into the acidification and anaerobic treatment tank; wherein the upper space of the tank is an acidification zone and the lower space thereof is an anaerobic decomposition zone; in the acidification and anaerobic treatment tank, the acidification zone comprises a dry acidified layer located above a liquid level and a wet acidified layer located below the liquid level; and the anaerobic decomposition zone comprises a floatation layer on the upper part of the anaerobic decomposition zone, a turbid liquid layer on the middle of the anaerobic decomposition zone and a heavy sediment layer on the lower part of the anaerobic decomposition zone; wherein a unidirectional feed inlet is provided in the tank corresponding to the upper portion of the acidification zone, from which the wastes are evenly sprayed on the top surface of the acidification zone; wherein a heavy materials discharge port is provided at the bottom of the anaerobic decomposition zone, through which the heavy materials are conveyed to the sediment washing device; wherein a first solid-liquid outlet is provided at the lower part of the anaerobic decomposition zone and a second solid-liquid outlet is provided at the middle-to-upper part of the anaerobic decomposition zone; a biogas outlet is provided in the top of the tank and connected to the biogas gathering tank through pipes; and a liquid inlet is also provided in the tank;

selection and separation step performed in an airtight space of conveying the materials discharged from the first and second solid-liquid outlets of the acidification and anaerobic treatment tank into a selection device in which solid wastes are grinded, anaerobic organic wastes are further crushed and plastics and chemical fibers after washing are screened and recycled; wherein the biogas slurry mixed with wastes which are not fully anaerobically decomposed is transferred into the next step;

buffering and adjusting step of temporarily storing the biogas slurry mixed with anaerobic wastes in a buffering and adjusting pool, wherein a liquid inlet for receiving the biogas slurry from the above step, a supplement liquid port for receiving the liquid from other steps, a water inlet for receiving supplement water from outside and a liquid outlet for providing liquid for the next step are provided in the buffering and adjusting pool; and wherein this step is performed in an airtight space in which a biogas outlet is provided and connected to the biogas gathering tank through pipes;

additional anaerobic treatment step of anaerobically treating the biogas slurry transferred from the above step in the additional anaerobic treatment tank wherein a biogas outlet is provided in the top of the additional anaerobic treatment tank and is connected to the biogas gathering tank through pipes; wherein a sludge outlet is provided at the bottom of the additional anaerobic treatment tank and is connected to a sludge sedimentation tank; wherein a supernatant liquid outlet is provided in the upper part of the additional anaerobic treatment tank and is connected to a biogas discharge tank or the acidification and anaerobic treatment tank through pipes; wherein the supernatant liquid through the biogas discharge tank is fed back to the previous step in which liquid is needed to be supplemented; wherein the gas outlet of the biogas discharge tank is connected to the biogas gathering tank through pipes;

sludge sedimentation and concentration step of sedimentating the sludge from the above step in the sludge sedimentation tank; wherein a supernatant liquid in the sludge sedimentation tank is fed back to the buffering and adjusting pool; the sedimentated sludge is taken out and recycled, and the sludge is dried for fertilizers or fuel coal preparation; wherein this step is performed in an airtight space, and a biogas outlet is provided in the airtight space and is connected to the biogas gathering tank through pipes.

As a preferred technical solution, an auxiliary crushing step and an auxiliary elutriation and floatation step are at least added once after the primary crushing step and the primary elutriation and floatation step, wherein:

the auxiliary crushing step of further crushing the transferred wastes with smaller specific gravity; wherein the residual organic wastes are crushed into slurry, the solid wastes are made smaller and inorganic wastes in the refuses are taken apart from the organic wastes in the refuses in order to facilitate the separation of organic wastes from inorganic wastes in the next step; the solid wastes are sized to be conveyed by the sediment conveying means in the secondary elutriation and floatation step and waste plastics and waste textiles are sized to be screened and separated in the subsequent procedures;

the auxiliary elutriation and floatation step of aerating and elutriating the wastes transferred from the above step in the secondary elutriation and floatation pool; wherein the solid wastes with larger specific gravity at the bottom of the elutriation and floatation pool are transferred into a sediment washing device by the sediment conveying means and are recycled after washing; wherein the wastes with smaller specific gravity in the elutriation and floatation pool are transferred into the next step by a floats conveying means and wherein the secondary elutriation and floatation fluids containing the organic wastes slurry are conveyed to the acidification and anaerobic treatment tank through pipes.

As an improvement of the above technical solutions, the sediment conveying means may be a screw conveyor and the floats conveying means may be a screw conveyor.

As an improvement of the above technical solutions, the sediment washing device is a sand washer and washing liquor from the sand washer is transferred into the acidification and anaerobic treatment tank through pipes.

As an improvement of the above technical solutions, the sediment after washing is conveyed into a building material workshop for manufacturing building materials.

As a preferred technical solution, an auxiliary magnetic separation step is further comprised after the primary crushing step, wherein the refuses processed by the primary crushing step are magnetically separated additionally, and the remaining steel scraps are separated from the refuses and are recycled.

As a preferred technical solution, an auxiliary magnetic separation step is further comprised before the acidification and anaerobic treatment step, wherein the refuses are magnetically separated additionally before they enter into the acidification and anaerobic treatment tank, and the remaining steel scraps are separated from the refuses and are recycled.

As a preferred technical solution, all the processing steps are performed in an enclosed workshop by the related equipments. The biogas gathering tank and the gas generator set may be located outside of the enclosed workshop in which a plurality of negative pressure mixed air collection ports are provided and are connected to the gas inlet of the gas generator set through pipes.

As an improvement of the above technical solutions, the negative pressure mixed air collection ports are provided at places where odors are produced in the workshop and/or at places where odors are emitted outward the workshop.

As an improvement of the above technical solutions, a mixed gas jar of biogas and air is provided in the selection device in the selection and separation step. The mixed gas outlet of the mixed gas jar is connected to the gas inlet of the gas generator set through pipes.

As a preferred technical solution, a biogas slurry heating device is provided in the buffering and adjusting pool in the buffering and adjusting step so as to speed up the anaerobic treatment in subsequent steps.

As an improvement of the above technical solution, a heating agent of the biogas slurry heating device is cooling water from the gas generator set and/or exhausts from the gas generator set.

As a preferred technical solution, a die-cutting method is used to cut wastes in the uniform cutting step.

As a preferred technical solution, the first and second solid-liquid outlets are opened alternatively in the acidification and anaerobic treatment step.

As a preferred technical solution, the biogas in the supernatant liquid escapes by spraying in the biogas discharge tank in the additional anaerobic treatment step.

As a preferred technical solution, plastics and chemical fibers selected in the selection and separation step are cracked and used for fuel oil preparation.

As a preferred technical solution, water required in the resource utilizing method of refuses in urban and rural areas is from sewage or wastewater with higher COD.

As a preferred technical solution, the sludge taken from said sludge sedimentation and concentration step is dried for fertilizers and fuel coal preparation.

As a result of these technical solutions, no direct workers involvement is needed from the beginning of the waste treatment. Instead, steel scraps are magnetically separated and recycled; inorganic wastes are separated by floatation, aeration and elutriation for recycling; most of anaerobic wastes after crushing, elutriation and flotation enter into the acidification and anaerobic treatment tank with the elutriation flotation fluid; the remaining anaerobic wastes and plastics, textiles attached to the anaerobic wastes are cut and put into the acidification and anaerobic treatment tank. In the acidification and anaerobic treatment tank, the anaerobic wastes are acidified and subject to the initial anaerobic reaction. Part of the energy in the anaerobic wastes is extracted. The anaerobic wastes adhered to plastics and chemical fibers are also acidified and peeled off and therefore are easily sorted out in the subsequent selection and separation step. In the additional anaerobic treatment tank, the wastes residue is subject to complete anaerobic reaction, and the energy contained in the anaerobic wastes is further released and converted into biogas. After the end of the waste treatment, the sludge may be made into fertilizers or fuel coal. During the whole process of the invention, resources contained in the refuses are gradually separated or released and collected. Until the process is completed, there is no discharge of pollutants. Further, the refuses need not be pre-sorted since the sorting and selection of the refuses are made throughout the overall process of the inventive refuses utilizing method. Thus, the biggest bottleneck of the constraints in refuses disposal is removed to render the present invention good practicality. No additional processing cost is incurred but significant economic benefits are achieved. The present invention can make the anaerobic treatment method continuatively dispose the refuses and thus can process a large amount of refuses. The present invention can also thoroughly solve the problem that the non-anaerobic refuses such as waste plastics, waste fibers etc. can't be recycled and therefore resources in the refuses may be completely recycled.

BRIEF DESCRIPTION OF THE DRAWINGS

FIG. 1 is a flow chart of an embodiment of the invention.

DETAILED DESCRIPTION

The invention will be further discussed in conjunction with the accompanying drawing and the embodiments below. In the following description, some example embodiments of the invention are set forth only by way of explanation. However, it will be apparent to those skilled in the art that the various embodiments may be modified in the various manners without departing from the spirit and scope of the invention. Therefore, the accompanying drawing and the description are illustrative in nature and not intended to limit the scope of the claims.

As shown in the figure, according to a resource utilizing method of refuses in urban and rural areas, an acidification and anaerobic treatment tank, an additional anaerobic treatment tank, a biogas gathering tank and a gas generator set are provided, wherein a gas inlet of said gas generator set is connected to the biogas gathering tank through pipes. In this embodiment, all the processing steps are performed in an enclosed workshop by the related equipments. The biogas gathering tank and the gas generator set are located outside of the enclosed workshop. A plurality of negative pressure mixed air collection ports are provided in the enclosed workshop and connected to the gas inlet of the gas generator set through pipes. The negative pressure mixed air collection ports are provided at places where odors are produced and also at places where odors are emitted outward in the walls of the workshop (for example, the windows). Thus, polluted air in the enclosed workshop is collected and burns in the gas generator set. The enclosed workshop is relatively enclosed and outside air is continuously supplemented into the enclosed workshop through gaps and slits. Thereby, the entire treatment plant does not emit odor, thus completely solving the problem of odor nuisance. Thus, the limitation of the waste disposal plant location is overcome.

The basic steps of the embodiment are described in detail below.

Step 1, i.e., refuses reception step: urban and rural refuses collected by garbage trucks are unloaded into a refuses hopper or a refuses silo. There are two gates through which garbage trucks go in and out of the enclosed workshop. Firstly, the outer gate is opened and the inner gate is kept close. At this time, the garbage truck enters. Then, when the outer gate is closed and the inner gate is opened, the garbage truck unloads. After the refuses are unloaded, the inner gate is closed and the outer gate is opened. The garbage truck drives out. Thus, it is ensured that no odor escapes outside during the unloading process.

Step 2, i.e., uniform refuses distribution step: the refuses in the refuses hopper or the refuses silo are uniformly transferred to the subsequent steps in order to ensure subsequent steps to be carried out continuously and to prevent the blocking and interruption of subsequent steps. In this step, the garbage bags in the refuses hopper or the refuses silo are torn, large waste plastics, waste timbers, textile wastes are torn and cut and inorganic wastes which are not able to be torn as well as organic wastes are separated from the refuses. Then, the torn and cut refuses are uniformly transferred to the next step. The volume of the processed solid wastes in this step is guaranteed to meet the requirements of a crusher in the primary crushing step. The biggest problem of waste disposal is existence of waste plastics and fibers because the conventional crusher does not work for them and they may cause the crusher to be wrapped and damaged. If the crushing is directly performed, the garbage bags cannot be opened and thus large refuses cannot be fed into, which causes the blocking and interruption of processing.

Step 3, i.e., primary magnetic separation step: the refuses transferred from the above step are magnetically separated. Steel scraps are separated from the refuses to facilitate the subsequent crushing process and to prevent steel scraps from damaging the crusher in the primary crushing step. Further, steel scraps may be recycled. Since the steels are extremely hard and have certain plasticity, it is easy to damage the crusher.

Step 4, i.e., primary crushing step: the refuses transferred from the above step are further crushed. The waste plastics and the waste textiles are cut into pieces, the steel scraps covering solid wastes are separated and some organic wastes are crushed into slurry. Thus, the solid wastes become smaller so that they may be conveyed by a sediment conveying means in the primary floatation step. In addition, it is ensured that waste plastics and the waste textiles may be screened and separated in the subsequent procedures. In the prior art, some anaerobic waste treatment methods use a pulverization method. Waste plastics and waste textiles are crushed into fine powders and can neither be anaerobically treated nor be separated, which renders a waste of resource. The residues after processing cause new pollution of soil.

Step 5, i.e., secondary magnetic separation step (auxiliary magnetic separation step): the refuses transferred from the above step are magnetically separated additionally. The remaining steel scraps in the wastes are separated from the wastes and are recycled.

Step 6, i.e., primary elutriation and floatation step: the refuses transferred from the above step are put into a primary elutriation and floatation pool and are aerated and elutriated. The solid wastes with larger specific gravity at the bottom of the elutriation and floatation pool are transferred into a sand washer by the screw conveyor and are recycled after washing, for example, transferring to a building material workshop for manufacturing building materials. The wastes with smaller specific gravity in the elutriation and floatation pool are transferred into the next step by the screw conveyor. The primary elutriation and floatation fluids containing the organic wastes slurry are conveyed to the acidification and anaerobic treatment tank through pipes.

Step 7, i.e., secondary crushing step (auxiliary crushing step): the transferred wastes with smaller specific gravity are further crushed. The residual organic wastes are partly crushed into slurry. The solid wastes are made smaller. Inorganic wastes for wrapping organic wastes are taken apart from the organic wastes in order to facilitate the separation of organic wastes from inorganic wastes in the next step. It is ensured that the solid waste may be conveyed by the screw conveyor in the secondary elutriation and floatation step and waste plastics and the waste textiles may be screened and separated in the subsequent procedures.

Step 8, i.e., secondary elutriation and floatation step (auxiliary elutriation and floatation step): the refuses transferred from the above step are put into the secondary elutriation and floatation pool and are aerated and elutriated. The solid wastes with larger specific gravity at the bottom of the elutriation and floatation pool are transferred into a sediment washing device by the sediment conveying means and are recycled after washing. The wastes with smaller specific gravity in the elutriation and floatation pool are transferred into the next step by a floats conveying means. The secondary elutriation and floatation fluids containing the organic wastes slurry are conveyed to the acidification and anaerobic treatment tank through pipes.

Step 9, i.e., uniform cutting step: the wastes with smaller specific gravity from the above step are further cut so that long strips of the wastes are fully cut into pieces. In other words, long strips of the wastes are selected from the wastes with smaller specific gravity transferred from the above step and are further cut into pieces. Thus, long strips of the wastes are fully cut into pieces so as to avoid the pipes to be blocked during the material transportation in the subsequent steps and to ensure the effective separation of plastics and chemical fibers after acidification and anaerobic treatment. After the above continuous processing steps, the refuses in this step includes all the plastics and textiles and some anaerobic wastes (most of anaerobic wastes are crushed and are conveyed into the acidification and anaerobic treatment tank via the floatation). In order to prevent the blocking of the pipes in the subsequent steps and to facilitate the screening and separation of the plastics and the chemical fibers in the subsequent steps, the die-cutting method is used to make the three-dimensional sizes of the wastes within given ranges. Thus, long strips of plastics and textiles are substantially eliminated.

Step 10, i.e., three-level magnetic separation step (auxiliary magnetic separation step): the refuses transferred from the above step are magnetically separated again. The remaining steel scraps in the refuses are separated and are recycled.

Step 11, i.e., acidification and anaerobic treatment step: the refuses transferred from the above step are transferred into the acidification and anaerobic treatment tank. The upper space of the tank is an acidification zone. The lower space of the tank is an anaerobic decomposition zone. In the acidification and anaerobic treatment tank, the acidification zone comprises a dry acidified layer located above the liquid level and a wet acidified layer located below the liquid level. The anaerobic decomposition zone comprises a floatation layer on the upper part of the anaerobic decomposition zone, a turbid liquid layer on the middle of the anaerobic decomposition zone and a heavy sediment layer on the lower part of the anaerobic decomposition zone. A unidirectional feed inlet is provided in the tank corresponding to the upper portion of the acidification zone. The wastes from the unidirectional feed inlet are evenly spilled on the top surface of the acidification zone. A heavy materials discharge port is provided at the bottom of the anaerobic decomposition zone. The heavy materials discharged through the heavy materials discharge port are conveyed to the sediment washing device. A first solid-liquid outlet is provided at the lower part of the anaerobic decomposition zone and a second solid-liquid outlet is provided at the middle-to-upper part of the anaerobic decomposition zone. A biogas outlet is provided in the top of the tank and connected to the biogas gathering tank through pipes. A liquid inlet is also provided in the tank. The acidification and anaerobic treatment tank of the invention mainly functions to make the wastes acidify. Further, the invention has the advantages of both the anaerobic dry fermentation method and the anaerobic wet fermentation method. The anaerobic dry fermentation method is conductive to acidification but is not conductive to anaerobic reaction due to ventilation. The anaerobic wet fermentation method is not conductive to acidification but is conductive to anaerobic reaction due to no direct contact with air. Neither of the methods can make acidification and anaerobic reaction get the best play. In the invention, the acidification zone comprises the dry acidification layer above the liquid level and the wet acidification layer below the liquid level. The refuses are fully and efficiently acidified in the dry acidification layer and then generate heat. The refuses are further acidified in the wet acidification layer and fall down into the anaerobic decomposition zone. In the anaerobic decomposition zone, the refuses are subject to preliminary anaerobic reaction and turn into biogas slurry. Some refuses with smaller specific gravity, such as wood brick and polyfoam, are floating under the bottom surface of the wet acidification layer and may be discharged through the second solid-liquid outlet after a certain time. In this step, the first and second solid-liquid outlets are opened alternatively so as to ensure that turbulence does not occur in the acidification and anaerobic treatment tank or destroy the layered distribution structure of materials in the tank.

Step 12, i.e., selection and separation step: the materials discharged from the first and second solid-liquid outlets of the acidification and anaerobic treatment tank are conveyed into a selection device in which solid wastes are grinded, anaerobic organic wastes are further crushed and plastics and chemical fibers after washing are screened and recycled. The biogas slurry mixed with wastes which are not fully anaerobically decomposed is transferred into the next step. This step is performed in an airtight space. A mixed gas jar of biogas and air is provided in the selection device. The mixed gas outlet of the mixed gas jar is connected to the gas inlet of the gas generator set through pipes. Plastics and chemical fibers selected in this step are cracked and used for fuel oil preparation.

Step 13, i.e., buffering and adjusting step: the biogas slurry mixed with anaerobic wastes is temporarily stored in a buffering and adjusting pool. A liquid inlet for receiving the biogas slurry from the above step, a supplement liquid port for receiving the liquid from other steps, a water inlet for receiving supplement water from outside and a liquid outlet for providing liquid for the next step are provided in the buffering and adjusting pool. This step is performed in an airtight space. A biogas outlet is provided in the airtight space and is connected to the biogas gathering tank through pipes. The heating agent of the biogas slurry heating device in this step is cooling water from the gas generator set and exhausts from the gas generator set. The biogas slurry heating device may be any one of well-known heat exchangers.

Step 14, i.e., additional anaerobic treatment step: the biogas slurry transferred from the above step is loaded into the additional anaerobic treatment tank and is anaerobically treated. A biogas outlet is provided in the top of the additional anaerobic treatment tank and is connected to the biogas gathering tank through pipes. A sludge outlet is provided at the bottom of the additional anaerobic treatment tank and is connected to a sludge sedimentation tank. A supernatant liquid outlet is provided in the upper part of the additional anaerobic treatment tank and is connected to a biogas discharge tank or the acidification and anaerobic treatment tank through pipes. The supernatant liquid through the biogas discharge tank is fed back to the previous step in which liquid is needed to be supplemented. The gas outlet of the biogas discharge tank is connected to the biogas gathering tank through pipes. In this step, energy contained in organic wastes in the refuses is completely released.

Step 15, i.e., sludge sedimentation and concentration step: the sludge from the above step is loaded into the sludge sedimentation tank and is sedimentated. A supernatant liquid in the sludge sedimentation tank is fed back to the buffering and adjusting pool. The sedimentated sludge is taken out and recycled. For example, the sludge is dried for fertilizers or fuel coal preparation. This step is performed in an airtight space. A biogas outlet is provided in the airtight space and is connected to the biogas gathering tank through pipes.

In this embodiment, the water required in the above steps and related devices results from sewage or wastewater with higher COD. Thus, water consumption is avoided and some wastewater is dealt with. Accordingly, the invention has significant technical progress.

In the present invention, the refuses need not be pre-sorted since the sorting and selection of the refuses are made throughout the overall process of the inventive refuses utilizing method. Thus, the biggest bottleneck of the constraints in refuses disposal is removed to render the present invention good practicality. No additional processing cost is incurred but significant economic benefits are achieved. The present invention can make the anaerobic treatment method continuatively dispose the refuses and thus can process a large amount of refuses. The present invention can also thoroughly solve the problem that the non-anaerobic refuses such as waste plastics, waste fibers etc. can't be recycled and therefore resources in the refuses may be completely recycled.

The principle, the features and the advantages of the present invention are shown and described above. It should be appreciated for persons skilled in the art that the present invention is not limited by the above embodiments, which only show the principle of the present invention. Various changes and modifications could be made herein without departing from the spirit and scope of the invention, which fall into the scope of the claimed invention. The scope of the invention is defined by the appended claims and equivalents thereof.

What is claimed is:

1. A method of utilizing refuses in urban and rural areas, wherein an acidification and anaerobic treatment tank, an additional anaerobic treatment tank, a biogas gathering tank and a gas generator set are provided and wherein a gas inlet of the gas generator set is connected to the biogas gathering tank through pipes, the method comprises the following steps:

(a) refuse collection step of unloading collected refuses into a refuse hopper or a refuse silo;
(b) distribution step, wherein garbage bags in the refuse hopper or the refuse silo are torn, large waste plastics, waste timbers and textile wastes are torn and cut and inorganic wastes and organic wastes which are not able to be torn are separated from the refuses; the torn and cut refuses are then transferred to a place where primary magnetic separation step is carried out;
(c) primary magnetic separation step of magnetically separating steel scraps from the refuses transferred from the distribution step wherein the steel scraps separated from the refuses are recycled;
(d) primary crushing step of crushing the refuses transferred from the primary magnetic separation step; wherein waste plastics and textile waste are further cut into pieces, steel scraps remained in the refuses covering solid wastes are separated and organic wastes remained in the refuses are crushed into slurry;
(e) primary elutriation and floatation step of putting the refuses transferred from the primary crushing step into a primary elutriation and floatation pool and performing aeration and elutriation; wherein solid wastes at the bottom of the primary elutriation and floatation pool are transferred into a sediment-washing device by sediment-conveying means and are recycled after washing; wastes with smaller specific gravity than that of the floatation fluid in the elutriation and floatation pool are transferred into a place where cutting step is carried out by floats-conveying means; and primary elutriation and floatation fluids containing organic waste slurry are conveyed to an acidification and anaerobic treatment tank through pipes;
(f) cutting step of cutting the wastes with smaller specific gravity than that of the floatation fluid from the primary elutriation and floatation step so that long strips of wastes are fully cut into pieces; or alternatively separate the long strips of wastes from the wastes with smaller specific gravity and cut separated long strips of wastes into pieces;
(g) acidification and anaerobic treatment step of transferring the refuses from the cutting step into the acidification and anaerobic treatment tank in which the refuses are combined with the primary elutriation and floatation fluids from the primary elutriation and floatation step and subjected to the acidification and anaerobic treatment; wherein upper space of the tank is an acidification zone and lower space thereof is an anaerobic decomposition zone; in the acidification and anaerobic treatment tank, the acidification zone comprises a dry acidified layer and a wet acidified layer; and the anaerobic decomposition zone comprises a floatation layer on a upper part of the anaerobic decomposition zone, a turbid liquid layer on the middle of the anaerobic decomposition zone and a heavy sediment layer on a lower part of the anaerobic decomposition zone; wherein a unidirectional refuse inlet is provided in the tank corresponding to upper portion of the acidification zone, from which the refuses are evenly spilled on the top of the acidification zone; wherein a heavy materials discharge port is provided at the bottom of the anaerobic decomposition zone, through which heavy materials are conveyed to the sediment-washing device; wherein a first solid-liquid outlet is provided at the lower part of the anaerobic decomposition zone and a second solid-liquid outlet is provided at a middle-to-upper part of the anaerobic decomposition zone; a biogas outlet is provided in the top of the tank and connected to the biogas gathering tank through pipes; and a liquid inlet is provided in the tank, wherein materials are discharged from the first and second solid-liquid outlets after the refuses are treated in the acidification and anaerobic treatment tank, and wherein discharged materials comprise biogas slurry and solid wastes;

(h) selection and separation step performed in an airtight space of conveying the materials discharged from the first and second solid-liquid outlets of the acidification and anaerobic treatment tank into a selection device in which the solid wastes are grinded, organic wastes in the solid wastes are also grinded, and plastics and chemical fibers are separated from the materials and are screened and recycled after washing; wherein the biogas slurry, mixed with grinded solid wastes which are not fully anaerobically decomposed, is transferred into a place where temporarily storing step is carried out;

(i) temporarily storing step of temporarily storing the biogas slurry mixed with the grinded solid waste which are not fully anaerobically decomposed in a buffering and adjusting pool, wherein a liquid inlet for receiving the biogas slurry mixed with the grinded solid waste from the selection and separation step, a supplement liquid port for receiving liquid from sludge sedimentation and concentration step, a water inlet for receiving water from outside and a liquid outlet for providing liquid for additional anaerobic treatment step are provided in the buffering and adjusting pool; and wherein the temporarily storing step is performed in an airtight space in which a biogas outlet is provided and connected to the biogas gathering tank through pipes;

(j) additional anaerobic treatment step of anaerobically treating the biogas slurry mixed with the grinded solid waste transferred from the temporarily storing step in the additional anaerobic treatment tank wherein a biogas outlet is provided in the top of the additional anaerobic treatment tank and is connected to the biogas gathering tank through pipes; wherein a sludge outlet is provided at the bottom of the additional anaerobic treatment tank and is connected to a sludge sedimentation tank; wherein a supernatant liquid outlet is provided in an upper part of the additional anaerobic treatment tank and is connected to a biogas discharge tank or the acidification and anaerobic treatment tank through pipes; wherein a gas outlet of the biogas discharge tank is connected to the biogas gathering tank through pipes;

(k) sludge sedimentation and concentration step of sedimentating sludge from the additional anaerobic treatment step in the sludge sedimentation tank; wherein a supernatant liquid in the sludge sedimentation tank is fed back to the buffering and adjusting pool; the sedimentated sludge is taken out and recycled; wherein the sludge sedimentation and concentration step is performed in an airtight space, and a biogas outlet is provided in the airtight space and is connected to the biogas gathering tank through pipes.

2. The method of claim 1, further comprising (l) an auxiliary crushing step and (m) an auxiliary elutriation and floatation step at least once after the primary crushing step and the primary elutriation and floatation step, wherein:

the auxiliary crushing step of further crushing the wastes with smaller specific gravity than that of the flotation fluid transferred from the primary elutriation and floatation step; wherein residual organic wastes are crushed into slurry, solid wastes are made smaller and inorganic wastes are taken apart from the residual organic wastes that wrap the inorganic wastes to facilitate separation of the residual organic wastes from the inorganic wastes in the (m) step; wherein the solid wastes are sized to be conveyed by the sediment-conveying means in the (m) step and the waste plastics and waste textiles are sized to be screenable and separable;

the auxiliary elutriation and floatation step of aerating and elutriating wastes transferred from the auxiliary crushing step in an auxiliary elutriation and floatation pool; wherein solid wastes at the bottom of the elutriation and floatation pool are transferred into a sediment-washing device by the sediment-conveying means and are recycled after washing; wherein wastes with smaller specific gravity than that of the floatation fluid in the elutriation and floatation pool are transferred to the place where the cutting step is carried out into next step by floats-conveying means and wherein auxiliary elutriation and floatation fluids containing organic waste slurry are conveyed to the acidification and anaerobic treatment tank through pipes.

3. The method of claim 1, wherein the sediment-conveying means is a screw conveyor and the floats-conveying means is a screw conveyor.

4. The method of claim 1, wherein the sediment-washing device is a sand washer and washing liquor from the sand washer is transferred into the acidification and anaerobic treatment tank through pipes.

5. The method of claim 1, wherein the solid wastes from the bottom of the primary elutriation and floatation pool after washing is conveyed into a building material workshop for manufacturing building materials.

6. The method of claim 1, further comprising (n) an auxiliary magnetic separation step after the primary crushing step, further magnetically separating the refuses processed by the primary crushing step, wherein residual steel scraps are separated from the refuses and are recycled.

7. The method of claim 1, further providing a biogas slurry heating device in the buffering and adjusting pool in the temporarily storing step so as to speed up anaerobic reactions in the additional anaerobic treatment step.

8. The method of claim 7, wherein a heating agent of the biogas slurry heating device is cooling-water from the gas generator set and/or exhausts from the gas generator set.

9. The method of claim 1, wherein the first and second solid-liquid outlets are opened alternatively in the acidification and anaerobic treatment step.

10. The method of claim 1, wherein the plastics and chemical fibers selected in the selection and separation step are cracked.

11. The method of claim 1, wherein water required in the method of utilizing refuses in urban and rural areas is from sewage or wastewater with high Chemical Oxygen Demand (COD).

12. The method of claim 1, wherein the sludge taken out from the sludge sedimentation and concentration step is dried for fertilizers or fuel coal preparation.

13. The method of claim 2, wherein the sediment-conveying means is a screw conveyor and the floats-conveying means is a screw conveyor.

14. The method of claim 2, wherein the sediment-washing device is a sand washer and washing liquor from the sand washer is transferred into the acidification and anaerobic treatment tank through pipes.

* * * * *